United States Patent
Burns et al.

(10) Patent No.: US 10,732,108 B2
(45) Date of Patent: Aug. 4, 2020

(54) FLUOROGENIC WATER SOLUBLE HYDRAZINE SENSORS

(71) Applicant: The Board of Trustees of the Leland Stanford Junior University, Stanford, CA (US)

(72) Inventors: Noah Burns, Stanford, CA (US); Steven R. Shuken, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/046,772

(22) Filed: Jul. 26, 2018

(65) Prior Publication Data
US 2019/0033215 A1    Jan. 31, 2019

Related U.S. Application Data

(60) Provisional application No. 62/538,589, filed on Jul. 28, 2017.

(51) Int. Cl.
*G01N 21/64* (2006.01)
*C07D 279/22* (2006.01)

(52) U.S. Cl.
CPC ....... *G01N 21/6428* (2013.01); *C07D 279/22* (2013.01)

(58) Field of Classification Search
CPC .................................................. C07D 279/22
See application file for complete search history.

(56) References Cited

U.S. PATENT DOCUMENTS

| 6,130,101 A | 10/2000 | Mao et al. |
| 2005/0090014 A1 | 4/2005 | Rao et al. |
| 2012/0178172 A1 | 7/2012 | Buvat et al. |

FOREIGN PATENT DOCUMENTS

| CN | 104109126 A | 10/2014 |
| GB | 869138 | * 6/1961 |
| IN | 200800241 | * 7/2010 |

OTHER PUBLICATIONS

Khan. Letters in Organic Chemistry, 2015, 12, 637-44 (Year: 2015).*
Reich. Handbook of Reagents for Organic Synthesis: Acidic and Basic Reagents, 1999, 169-173 (Year: 1999).*
Scapini. Ateneo Parmense, 1964, 35(4), 328-34 (Year: 1964).*
Choi, Myung Gil et al. (2011) "Hydrazine-Selective Chromogenic and Fluorogenic Probe Based on Levulinated Coumarin," *Organic Letters* 12(19):5260-5263.
Hughes, Laura D. et al. (Feb. 2014) "Choose Your Label Wisely: Water-Soluble Fluorophores Often Interact with Lipid Bilayers," *PLOS One* 9(2):1-8.
Sun, Mingda et al. (Jan. 2014) "A New Fluorescent and Colorimetric Sensor for Hydrazine and its Application in Biological Systems," *Journal of Materials Chemistry B* 1849-1851.
Zhang, Jianjian et al. (Aug. 2015) "Naked-Eye and Near-Infrared Fluorescence Probe for Hydrazine and Its Applications in In Vitro and In Vivo Bioimaging," *Analytical Chemistry* 9101-9107.

* cited by examiner

*Primary Examiner* — Noble E Jarrell
(74) *Attorney, Agent, or Firm* — Bret E. Field; Bozicevic, Field & Francis LLP

(57) ABSTRACT

Water soluble fluorogenic sensors for detecting a hydrazine analyte are provided. Aspects of the fluorogenic sensors include at least one water soluble group and a hydrazine reactive group. Methods of evaluating a sample for the presence of a hydrazine analyte and methods of detecting hydrazine diffusion across a phospholipid membrane are provided. Kits for practicing the subject methods are also provided.

23 Claims, 11 Drawing Sheets

FLUOROGENIC WATER SOLUBLE HYDRAZINE SENSORS

Hydrazine is a toxic but widely used industrial chemical. It is used as an intermediate in the chemical industry, for example, to produce plastic blowing agents, dyes, herbicides and pharmaceuticals. Because of its desirable physical characteristics, such as high boiling point, thermal stability, and spontaneous ignition with strong oxidizing agents, it is also used for rocket and jet propellants. Hydrazine is also known to be released in waste water treatment technologies and it is known to be produced in the body during drug metabolism.

Several toxic effects have been associated with exposure to hydrazine e.g. liver damage, hyperglycemia, neurodegeneration, and cancer. Due to its toxicity to humans, the Occupational Safety and Health Administration (OSHA) Permissible Exposure limit is 1 ppm, although the National Institute for Occupational Safety and Health (NIOSH) recommended exposure limit is 0.03 ppm.

A number of analytical techniques exist for detecting the presence of hydrazine in a sample, including but not limited to spectrometric, titrimetric, electrochemical, mass spectrometry (MS), and spectrophotometry methods. However, all of these methods are expensive, time consuming and impractical for real-time on-site analysis. Fluorogenic sensors also exist for the detection of hydrazine, but none of these are water soluble or operate at room temperature and at neutral pH.

Therefore, water soluble fluorogenic sensors for application in a variety of aqueous and biological samples are of interest.

SUMMARY

Fluorogenic water soluble hydrazine sensors, methods and kits for using the same are provided. The fluorogenic sensors are phenothiazine compounds including at least one water soluble group and a hydrazine reactive group. In some cases, the water soluble group is a sulfonic acid group or a salt thereof. The water soluble group may be included at one or more of a variety of positions. In some cases, the hydrazine reactive group may be an α,β-unsaturated α-cyanoamide group. In some cases the hydrazine reactive group may be an α,β-unsaturated malononitrile group.

Methods of detecting a hydrazine analyte in a sample are provided. Aspects of the method include, contacting a sample with a fluorogenic water soluble hydrazine sensor under conditions sufficient to react the hydrazine, if present, with the fluorogenic water soluble sensor to produce a fluorescent adduct. Aspects of the method further include detecting the fluorescence of the adduct.

Methods of detecting hydrazine diffusion across a phospholipid membrane are also provided. Aspects of the method include, contacting a cell with a fluorogenic water soluble hydrazine sensor and detecting a variation in intensity of fluorescence emitted by the compound when the cell is exposed to hydrazine in a medium which diffuses across the cell membrane.

Also provided are kits incorporating the fluorogenic water soluble hydrazine sensors of interest to facilitate their use in such methods.

BRIEF DESCRIPTION OF THE FIGURES

It is understood that the drawings, described below, are for illustration purposes only. The drawings are not intended to limit the scope of the present teachings in any way.

DEFINITIONS

Figure 1:
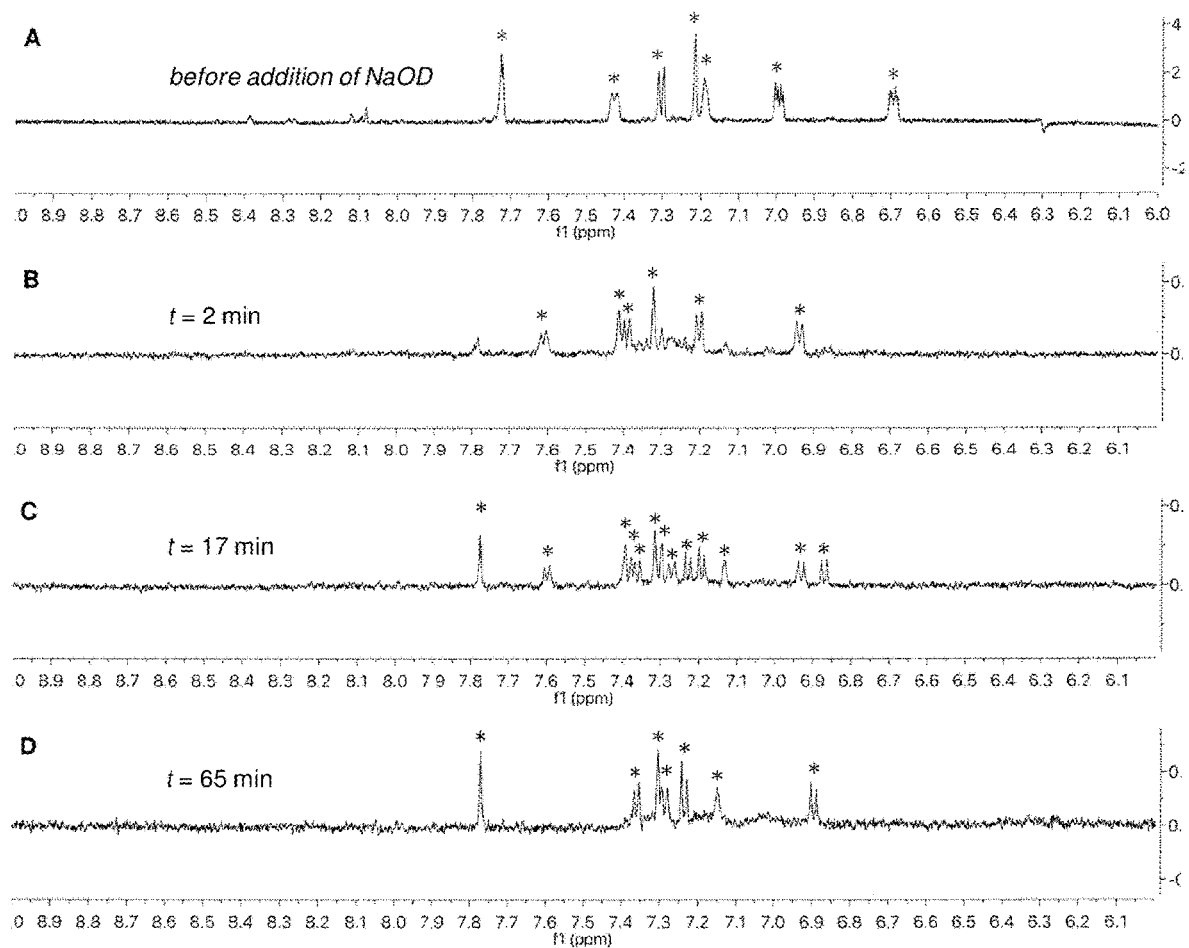
FIG. 1 (panels A to D) illustrates $^1$H NMR spectra (600 MHz, $D_2O$) acquired before and during NMR kinetic experiments: depicting hydrazine sensor, compound 2 (panel A); hydrazal 4 (t=2 min) (panel B); a mixture of hydrazal 4 and dimer 5 (t=17 min) (panel C); and azine compound 5 (t=65 min) (panel D).

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "sample" relates to a material or mixture of materials, in some cases in liquid form, containing one or more analytes of interest. In some embodiments the "sample" is a "water sample", such as an environmental water sample or a drinking water sample. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

As used herein the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Aryl" or "Ar" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachments is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =OR, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

Other definitions of terms may appear throughout the specification.

DETAILED DESCRIPTION

As summarized above, provided herein are fluorogenic water soluble hydrazine sensors and methods of making and using the same. Embodiments of each are described in more detail in the sections below.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, fluorogenic water soluble hydrazine sensors are described first in greater detail. Next, methods of interest in which fluorogenic water soluble hydrazine sensors find use are reviewed. Kits that may be used in practicing methods of the invention are also described.

Fluorogenic Water Soluble Hydrazine Sensors

As summarized above, the present disclosure provides fluorogenic water soluble hydrazine sensors. The subject fluorogenic sensors are phenothiazine compounds including at least one water soluble group and a hydrazine reactive group. The one or more water soluble groups may be included at any convenient positions to impart increased water solubility to the phenothiazine compound. The term "water soluble group" (WSG) refers to a group that is well solvated in aqueous environments and that imparts improved water solubility upon the molecules to which it is attached. In some instances, the compounds incorporate at least one charged group to increase water solubility. Any convenient charged groups may be incorporated. Charged groups of interest, include but are not limited to, a sulfonate, an ammonium, a carboxy, a phosphate, an amino, a substituted amino and the like. The term "sulfonate", by itself or as part of another group, refers to any compound or substituent that contains sulfonic acid, a salt thereof, e.g., one or more moieties having the following structure:

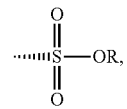

where R is hydrogen or a counter ion, such as a metal ion or ammonium ion. Similarly, by "carboxy" is meant carboxylic acid or salt of carboxylic acid. "Phosphate", as used herein, is an ester of phosphoric acid, and includes salts of phosphate. "Phosphonate", as used herein, means phosphonic acid and includes salts of phosphonate. WSG of interest include, but are not limited to, carboxylate, phosphonate, phosphate, sulfonate, sulfate, sulfinate, sulfonium, ester, polyethylene glycols (PEG) and modified PEGs, hydroxyl, amine, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups or glycols.

While the increase in solubility may vary, in some instances the increase (as compared to the compound without the WSG(s)) is 2 fold or more, e.g., 5 fold, 10 fold, 25 fold, 50 fold, 100 fold or more. In some embodiments, a WSG increases the solubility of the fluorogenic sensor compound in a predominantly aqueous solution, as compared to a control compound which lacks the WSG. In some instances, the WSGs of the fluorogenic sensor are non-ionic side groups capable of imparting solubility in water in excess of 10 mg/mL. The water solubilizing groups may be any convenient hydrophilic group that is well solvated in aqueous environments. In some cases, the hydrophilic water solubilizing group is charged, e.g., positively or negatively charged. In certain cases, the hydrophilic water solubilizing group is a neutral hydrophilic group. In some embodiments, the WSG is a hydrophilic polymer, e.g., a polyethylene glycol, a cellulose, a chitosan, or a derivative thereof. Multiple WSGs may be included in the subject fluorogenic sensors. In some embodiments, at least one WSG on the fluorogenic sensor is a sulfonate group.

As used herein, a "hydrazine reactive group", refers to a moiety on the phenothiazine compound that is capable of chemically reacting with hydrazine to produce a fluorescent adduct of the phenothiazine compound. A variety of hydrazine reactive groups may be utilized in the subject fluorogenic sensors, as described in greater detail below. Hydrazine reactive groups of interest include, but are not limited to, a disubstituted alkene, in which the alkene is substituted with two groups independently selected from a nitrile, an ester, an amide or a ketone. In some cases the alkene is substituted with a malononitrile group, a malonate ester group or a malonate amide group. The term "malonate ester" refers to esters of malonic acid $CH_2(C(O)OR')_2$, where the R' group of interest includes, but is not limited to, an alkyl group, substituted alkyl group, aryl group or substituted aryl group as defined herein. Similarly the term "malonate amide" refers to the amide of malonic acid $(CH_2(C(O)NR''_2)_2$, where the R'' groups of interest include, but are not limited to, a H, an alkyl group, a substituted alkyl group, an aryl group or substituted aryl group as defined herein. In certain cases, the hydrazine reactive group is an alkene substituted with a malononitrile group. In certain cases, the hydrazine reactive group is an alkene substituted with a nitrile group and an amide group. In some cases, the hydrazine reactive group is an α,β-unsaturated α-cyanoamide group. In some cases the hydrazine reactive group is an α,β-unsaturated malononitrile group. Hydrazine reactive groups of interest also include phenyl acetates, O-acyl phenols or aldehyde derivatives.

In some embodiments, the dye is described by Formula I:

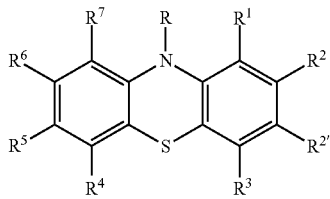

(I)

where, $R^1$ and $R^3$ are independently selected from H, alkyl, substituted alkyl, halogen, carboxy, sulfonate, phosphonate, carboxylate, cyano, hydroxyl, carboxyamide and sulfonamide; $R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine reactive group; $R^4$, $R^5$, $R^6$, $R^7$ are independently selected from H, sulfonate, phosphonate, carboxy, halogen, alkyl, substituted alkyl, cyano, hydroxyl, carboxyamide, sulfonamide and carboxylate; and R is alkyl or substituted alkyl; wherein at least one of $R^1$-$R^7$ is a water soluble group (e.g., as described herein), and at least one of $R^2$-$R^2$ is a hydrazine reactive group (e.g., ad described herein), or a salt thereof.

In some instances, in Formula I, at least one of $R^4$, $R^5$, $R^6$ and $R^7$ is a water soluble group, such as a sulfonate group. In certain instances, at least $R^6$ is a water soluble group, such as a sulfonate group. In some cases, at least one of $R^1$, $R^2$ and $R^3$ is a water soluble group. It is understood that any convenient water soluble group may be used in the subject compounds to provide for solubility of the subject hydrazine sensors in an aqueous environment.

In some embodiments, in Formula I, $R^2$ or $R^{2'}$ has the following structure

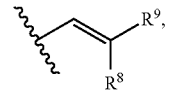

where $R^8$ and $R^9$ are each independently CN, $C(O)OR^{10}$, $C(O)NR^{11}_2$ and $C(O)R^{10}$, wherein $R^{10}$ is alkyl, substituted alkyl, aryl or substituted aryl and $R^{11}$ are each independently H, alkyl, substituted alkyl, aryl or substituted aryl. In certain embodiments, $R^8$ and $R^9$ are both CN. In certain embodiments, $R^8$ is CN and $R^9$ is $C(O)NH_2$. In some cases, $R^8$ is $C(O)NH_2$ and $C^9$ is CN.

In some cases, the R substituent on the nitrogen of the phenothiazine ring is an ethyl group. In some embodiments, the R group is an alkyl group or substituted alkyl group as defined herein.

In some instances, Formula (I) is of the formula (IA):

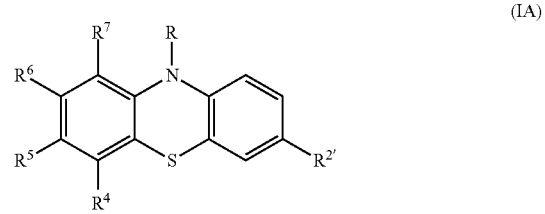

(IA)

where, $R^{2'}$ is a hydrazine reactive group (e.g., as described herein); $R^4$, $R^5$, $R^6$, $R^7$ are independently selected from H, sulfonate, phosphonate, carboxy, halogen, alkyl, substituted alkyl, cyano, hydroxyl, carboxyamide, sulfonamide and carboxylate; and R is alkyl or substituted alkyl; wherein at least one of $R^1$-$R^7$ is a water soluble group (e.g., as described herein), or a salt thereof.

In some instances, Formula (I) is of the formula (IB):

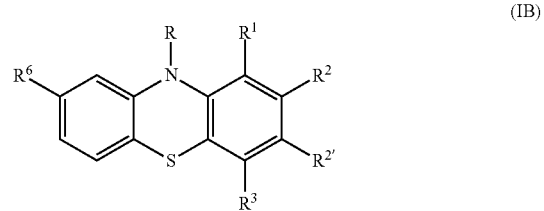

(IB)

where, $R^1$ and $R^3$ are independently selected from H, alkyl, substituted alkyl, halogen, carboxy, sulfonate, phosphonate, carboxylate, cyano, hydroxyl, carboxyamide and sulfonamide; $R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine reactive group; $R^6$ is a water soluble group (e.g., as described herein); and R is alkyl or substituted alkyl; wherein at least one of $R^2$-$R^2$ is a hydrazine reactive group (e.g., as described herein), or a salt thereof.

In some instances, Formula (I) is of the formula (IC):

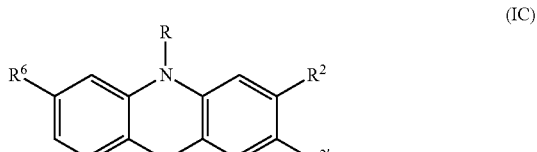
(IC)

where, $R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine reactive group; $R^6$ is a water soluble group (e.g., as described herein); and R is alkyl or substituted alkyl; wherein at least one of $R^2$-$R^{2'}$ is a hydrazine reactive group (e.g., as described herein), or a salt thereof.

In some instances, Formula (I) is of the formula (ID):

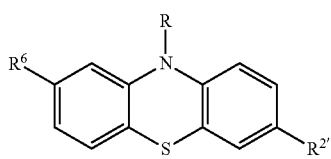
(ID)

where, $R^{2'}$ is a hydrazine reactive group (e.g., as described herein); $R^6$ is a water soluble group (e.g., as described herein); and R is alkyl or substituted alkyl, or a salt thereof.

It will be understood that any convenient water soluble group may be used in a compound of formulae (I)-(ID), as long as the group improves the solubility of the subject hydrazine sensors in an aqueous environment. Further, it will be understood that any convenient hydrazine reactive group may be used in a compound of formulae (I)-(ID), as long as the group capable of chemically reacting with hydrazine to produce a fluorescent adduct of the compound of formula (I)-(ID).

In some instances, Formula I has the structure of compound 2:

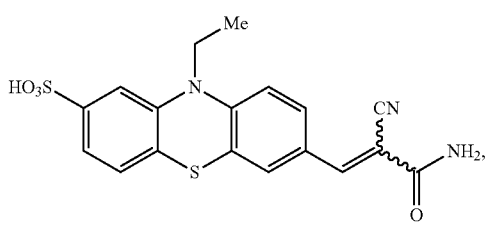
2 or a salt thereof.

In some embodiments, the alkene in compound 2 is the E isomer. In other embodiments, the alkene in compound 2 is the Z isomer.

In some instances, Formula I has the structure of compound 3:

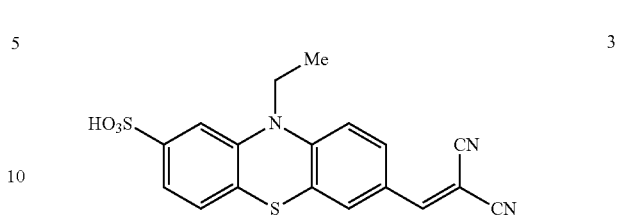
3

The subject fluorogenic sensors are configured to react with hydrazine to produce a fluorescent dye product which permits detection with high sensitivity. As used herein, the term "fluorogenic" refers to an acceptor moiety that is capable of demonstrating a change in fluorescence upon interaction with hydrazine. The fluorogenic sensor can have a non-fluorescent form or "off-state" in the absence of hydrazine and is capable of being converted to a fluorescent form or "on-state" in the presence of hydrazine. The reaction of the fluorogenic sensor with hydrazine (i.e., conversion of the sensor from an off-state to an on-state) can be achieved in a variety of methods via the direct or indirect action of hydrazine on the fluorogenic sensor (e.g., as described herein). As used herein, the term "off-state" refers to a first chemical or physical form of the water soluble fluorogenic sensor that exists in the absence of hydrazine. As used herein, the term "on-state" refers to a second chemical or physical form of the fluorogenic sensor that exists after the direct or indirect reaction of hydrazine on the fluorogenic sensor compound.

As used herein, the term "chemical form" refers to the chemical structure of a molecule, where the first and second forms of a fluorogenic sensor involve distinct chemical structures which can have different spectral properties. As used herein, the term "physical form" is meant to encompass a variety of different physical forms of a molecule having identical chemical structure, but having different spectral properties due to the molecule being in e.g., a different electronic state, a different steric state, or a different physical environment.

The subject fluorogenic sensors provide for a measurable fluorescence emission difference between the off-state and on-state of the sensor. As such, the hydrazine can be detected in a sample by observing an increase in fluorescence from the sensor. It is understood that, in some cases, the "off-state" or "non-fluorescent form" of the fluorogenic sensor itself may have some inherent fluorescence that is relatively small as compared to the fluorescence of the "on-state" or "fluorescent form" of the sensor.

In some cases, the fluorogenic sensor is ratiometric. As used herein, the term "ratiometric" refers to a composition containing a fluorogenic sensor for hydrazine where the intensity of the fluorescence emission signal obtained from the composition is proportional to the amount of hydrazine that is present. As such, measurement of the fluorescence emission signal can be used to quantitate the amount of hydrazine that is present in the composition.

When the fluorogenic sensor is in its off-state form, the compound is relatively non-fluorescent. Upon conversion of the fluorogenic sensor to a fluorescent sensor product (i.e., the on-state form of the sensor), a measurable fluorescence emission is detected.

The fluorogenic sensor in its "on-state" can have a quantum yield of 0.1 or more, such as a quantum yield of 0.15 or more, 0.2 or more, 0.25 or more, 0.3 or more, 0.35 or more, 0.4 or more, 0.45 or more, 0.5 or more or even more. In some instances, the sensor has an extinction coefficient of $5 \times 10^5$ $cm^{-1}M^{-1}$ or more, such as $6\times10^5$ $cm^{-1}M^{-1}$ or more, $7\times10^5$ $cm^{-1}M^{-1}$ or more, $8\times10^5$ $cm^{-1}M^{-1}$ or more, $9\times10^5$ $cm^{-1}M^{-1}$ or more, such as $1\times10^6$ $cm^{-1}M^{-1}$ or more, $1.5\times10^6$ $cm^{-1}M^{-1}$ or more, $2\times10^6$ $cm^{-1}M^{-1}$ or more, $2.5\times10^6$ $cm^{-1}M^{-1}$ or more, $3\times10^6$ $cm^{-1}M^{-1}$ or more, $4\times10^6$ $cm^{-1}M^{-1}$ or more, $5\times10^6$ $cm^{-1}M^{-1}$ or more, $6\times10^6$ $cm^{-1}M^{-1}$ or more, $7\times10^6$ $cm^{-1}M^{-1}$ or more, or $8\times10^6$ $cm^{-1}M^{-1}$ or more. In some embodiments, the sensor has a molar extinction coefficient of $5\times10^5$ $M^{-1}$ $cm^{-1}$ or more. In certain embodiments, the sensor has a molar extinction coefficient of $1\times10^6$ $M^{-1}$ $cm^{-1}$ or more.

The emission of the subject fluorogenic sensor in its "on-state" can have a brightness of 100 $mM^{-1}$ $cm^{-1}$ or more, 150 $mM^{-1}$ $cm^{-1}$ or more, 200 $mM^{-1}$ $cm^{-1}$ or more, 250 $mM^{-1}$ $cm^{-1}$ or more, 300 $mM^{-1}$ $cm^{-1}$ or more, 400 $mM^{-1}$ $cm^{-1}$ or more, 500 $mM^{-1}$ $cm^{-1}$ or more, 600 $mM^{-1}$ $cm^{-1}$ or more, 700 $mM^{-1}$ $cm^{-1}$ or more, 800 $mM^{-1}$ $cm^{-1}$ or more, 900 $mM^{-1}$ $cm^{-1}$ or more, 1,000 $mM^{-1}$ $cm^{-1}$ or more, or even more. In certain instances, the emission of the sensor in its "on-state" has a brightness that is at least 5-fold greater than the brightness of a directly excited fluorescent compound control, such as at least 10-fold greater, at least 20-fold greater, at least 30-fold greater, at least 50-fold greater, at least 100-fold greater, at least 300-fold greater, or even greater than the brightness of a directly excited fluorescent compound control.

In certain embodiments, the fluorogenic sensor has an absorption maximum wavelength of 525 nm or less, such as a wavelength of 500 nm or less, 450 nm or less, 440 nm or less, 430 nm or less, 420 nm or less, 410 nm or less, 400 nm or less, or even less. In certain instances, the fluorogenic sensor has an absorption maximum wavelength in the range of 300 nm to 400 nm. In certain instances, the fluorogenic sensor has an absorption maximum wavelength in the range of 400 nm to 450 nm. In certain instances, the fluorogenic sensor has an absorption maximum wavelength in the range of 450 nm to 500 nm. In certain instances, the fluorogenic sensor has an absorption maximum wavelength in the range of 500 nm to 550 nm. In some instances, the fluorogenic sensor has an emission maximum wavelength in the range of 375 nm to 900 nm (such as in the range of 380 nm to 900 nm, 390 nm to 900 nm, 400 nm to 900 nm, 450 nm to 900 nm, 500 nm to 900 nm, 525 nm to 900 nm, 550 nm to 900 nm, or 600 nm to 900 nm).

The subject fluorogenic sensor may have one or more desirable spectroscopic properties, such as a particular absorption maximum wavelength, a particular emission maximum wavelength, extinction coefficient, quantum yield, and the like. In some embodiments, the fluorogenic sensor has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of interest include, but are not limited to: 395 nm±5 nm, 460 nm±5 nm, 490 nm±5 nm, 550 nm±5 nm, 560 nm±5 nm, 605 nm±5 nm, 650 nm±5 nm, 680 nm±5 nm, 700 nm±5 nm, 805 nm±5 nm. In certain instances, the fluorogenic sensor has an emission maximum wavelength selected from the group consisting of 395 nm, 460 nm, 490 nm, 525 nm, 550 nm, 560 nm, 605 nm, 650 nm, 680 nm, 700 nm and 805 nm. In certain instances, the fluorogenic sensor has an emission maximum wavelength of 525 nm±5 nm.

In some instances, the fluorogenic sensor has an extinction coefficient of $5\times10^5$ $cm^{-1}M^{-1}$ or more, such as $6\times10^5$ $cm^{-1}M^{-1}$ or more, $7\times10^5$ $cm^{-1}M^{-1}$ or more, $8\times10^5$ $cm^{-1}M^{-1}$ or more, $9\times10^5$ $cm^{-1}M^{-1}$ or more, such as $1\times10^6$ $cm^{-1}M^{-1}$ or more, $1.5\times10^6$ $cm^{-1}M^{-1}$ or more, $2\times10^6$ $cm^{-1}M^{-1}$ or more, $2.5\times10^6$ $cm^{-1}M^{-1}$ or more, $3\times10^6$ $cm^{-1}M^{-1}$ or more, $4\times10^6$ $cm^{-1}M^{-1}$ or more, $5\times10^6$ $cm^{-1}M^{-1}$ or more, $6\times10^6$ $cm^{-1}M^{-1}$ or more, $7\times10^6$ $cm^{-1}M^{-1}$ or more, or $8\times10^6$ $cm^{-1}M^{-1}$ or more. In some embodiments, the fluorogenic sensor has a molar extinction coefficient of $5\times10^5$ $M^{-1}$ $cm^{-1}$ or more. In certain embodiments, the fluorogenic sensor has a molar extinction coefficient of $1\times10^6$ $M^{-1}$ $cm^{-1}$ or more.

Methods

As summarized above, aspects of the present disclosure include methods of evaluating a sample for the presence of a hydrazine. Aspects of the subject methods include contacting the sample with a fluorogenic sensor (e.g., as described herein) under conditions sufficient to react the hydrazine analyte, if present, with the fluorogenic sensor to produce a fluorescent adduct, and detecting the fluorescence of the adduct.

The sample is contacted with the subject fluorogenic sensor under conditions in which the sensor chemically reacts with the hydrazine analyte, if present. Conditions in which the sensor chemically selectively reacts with the hydrazine analyte include conditions where the sensor is chemically stable and does not react in the absence of hydrazine.

The fluorogenic sensor reacts with hydrazine, if present to produce a fluorescent adduct. In some embodiments, the presence of the fluorescent adduct is detected by detecting a change in intensity of the fluorescence emitted from the sample. In some cases, the change in intensity of the fluorescence emitted is detected at or near 525 nm.

In some embodiments, the fluorogenic sensor compound is orange in its "off state" and upon reaction with hydrazine analyte in a sample produces a colorless adduct in its "on-state" which fluoresces green when exposed to UV light.

The temperature at which the reaction of the fluorogenic sensor to the hydrazine analyte takes place is generally room temperature. However, the temperature may vary, and in some instances may range from 5° C. to 50° C., such as from 10° C. to 40° C., 15° C. to 40° C., 20° C. to 40° C., e.g., 20° C., 25° C., 30° C., 35° C. or 37° C. In certain instances, the temperature is 25° C., 30° C., 35° C. or 37° C. In certain cases, the temperature at which reaction takes place is room temperature (e.g., 25° C.), 30° C., 35° C. or 37° C.

The reaction of the fluorogenic sensor with hydrazine in a sample is generally fast. In some cases, the reaction of the fluorogenic sensor with the hydrazine adduct is complete in 1 hour or less, and can be visualized by a color change from orange to colorless upon completion of the reaction with hydrazine. In some instances, the reaction time may be 1 hour or less, such as 30 minutes (min) or less, 20 min or less, 10 min or less, 2 min or less, or 1 min or less. In certain cases, reaction of the fluorogenic sensor with hydrazine in a sample is complete in 2 min or less.

In certain instances, the fluorogenic sensor has the structure of compound 2, e.g., as described herein, and after reaction with hydrazine forms hydrazal 4:

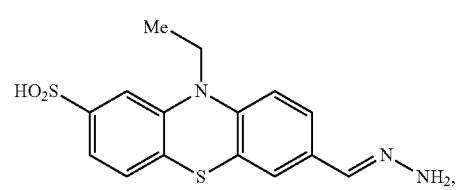

4 or a salt thereof.

In certain instances, the compound 2 initially reacts with hydrazine to form hydrazal 4 and subsequently forms a dimer, e.g., compound 5:

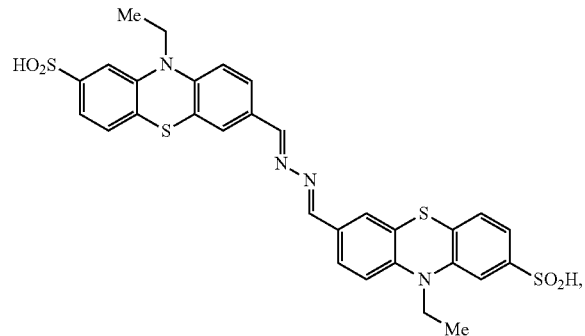

or a salt hereof.

In certain instances of the reaction of compound 2 with hydrazine, only hydrazal 4 is observed. In other instances, dimer 5 is observed as a mixture with hydrazal 4. In other instances of the reaction of compound 2 with hydrazine, only dimer 5 is observed.

The reaction of the fluorogenic sensor, compound 2, with hydrazine in a sample is generally fast. In some instances, compound 2 reacts with hydrazine in a sample to form hydrazal 4 in one hour or less, such as 30 min or less, 20 min or less, 10 min or less, 2 min or less, 1 min or even less. In some instances, hydrazal 4 is formed in 2 minutes or less and is the only adduct observed.

The reaction of hydrazal 4 to from dimer 5 is generally slow. In some instances, hydrazal 4 is converted to compound 5 after one hour or more, such as 60 min or more, 65 min or more, 70 min or more, 80 min or more, 90 min or even more. In some instances, a mixture of hydrazal 4 and compound 5 is observed in 15 min or more, such as 17 min or more, 20 min or more, 30 min or more, or even more.

The pH at which the reaction of the fluorogenic sensor to the hydrazine analyte takes place is generally neutral. However, the pH may vary, and in some cases may range from 6 to 8, such as from 6.1 to 6.5, 6.6 to 7.3, 7.4 to 7.8 e.g. 6.5, 7.0, 7.5. In certain cases the pH is neutral.

The term "sample" relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

Samples of interest for detecting the level of hydrazine present include, but are not limited to, water samples and biological samples. In some cases, the water sample may be an environmental water sample, such as a stream or aquifer. In certain embodiments, the environmental water sample includes treated or untreated water from a waste water treatment plant, or a water reservoir containing a town supply of water. In some cases, the water sample is a sample of drinking water.

In some embodiments, the sample is a biological sample, such as urine.

In some embodiments, the level of hydrazine analyst in the sample is quantitatively determined. In some embodiments, the fluorogenic sensor is added to the sample in a concentration of 4 mM or more, such as a concentration of 4.2 mM or more, 4.4 mM or more, 4.6 mM or more, 4.8 mM or more, 5.0 mM or more or even more. In some embodiments the fluorogenic sensor is added to the sample in a concentration of 420 µM or more, such as a concentration of 440 µM or more, 450 µM or more, 500 µM or more, 550 µM or more, 600 µM or more, 650 µM or more, 700 µM or more, 750 µM or more, 800 µM or more or even more. In some embodiments the fluorogenic sensor is added to the sample in a concentration of 440 µM or less, such as a concentration of 420 µM or less, 400 µM or less, 350 µM or less, 300 µM or less, 250 µM or less, 200 µM or less, 150 µM or less, 100 µM or less or even less.

Aspects of the subject methods also include a method of detecting hydrazine diffusion across a phospholipid membrane. Aspects of the subject methods include, contacting a cell with a fluorogenic sensor and detecting a variation of an intensity of fluorescence emitted by the fluorogenic sensor when the cell is exposed to hydrazine in a medium which diffuses across the cell membrane.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoietic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

In some embodiments, the phospholipid membrane, through which hydrazine diffusion is detected, comprises ladderane membranes. For example, ladderane lipids ([5][3] PC) of the following structure:

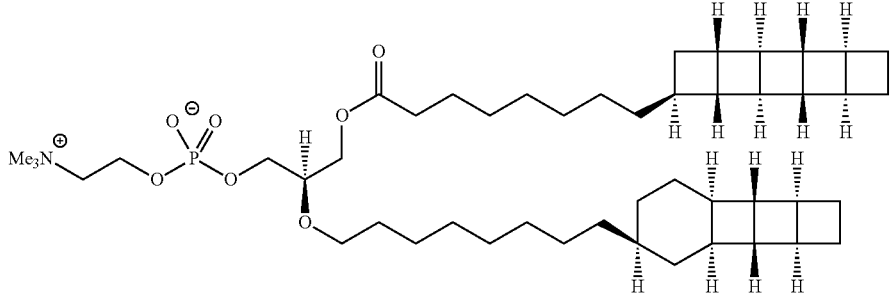

Without being bound to any particular theory, it was observed that when a conventional phospholipid membrane is replaced with a ladderane membrane hydrazine diffuses more slowly thorough the membrane, or does not diffuse through the membrane at all. In certain embodiments, the rate of diffusion of the fluorogenic sensor across the phospholipid membrane is also slow. In certain cases, hydrazine diffuses more slowly through a ladderane membrane than a conventional straight chain phospholipid membrane with a longer hydrophobic tail length than the said ladderane membrane. In some cases, the ladderane membrane is equally as permeable to hydrazine as a conventional straight chain phospholipid membrane of the same bilayer thickness. In some embodiments, the fluorogenic sensor does not interfere with the phospholipid membrane.

In some embodiments, the hydrazine diffusion across the phospholipid membrane is quantitatively determined. In some embodiments, the hydrazine is generated in the cell by a known drug.

Aspects of the subject methods include evaluating the sensor-contacted sample for fluorescence emission from the fluorogenic sensor to evaluate whether the hydrazine analyte is present in the sample. Once the sample has been contacted with the fluorogenic sensor, any convenient methods may be utilized in assaying the sensor-contacted sample that is produced for a ratiometric change in fluorescence. Evaluating the sensor-contacted sample can include detecting a fluorescent signal from the sample, if present, and comparing the signal to a control solution of sensor that contains no sample. Any convenient ratiometric methods that find use in detecting and quantitating fluorescence emissions from fluorogenic dyes can be utilized in the subject methods, such as those ratiometric methods described by, US Publication No. 20050090014.

In certain cases, the subject methods include evaluating the fluorogenic sensor-contacted sample over a period of time. The evaluating may be performed continuously or at discrete time points to produce a temporal evaluation of the sample over any convenient time frame. In some cases, the evaluating is performed over a period of 1 minute or more, such as 10 minutes or more, 30 minutes or more, 60 minutes or more, 3 hours or more, 6 hours or more, 12 hours or more, 24 hours or more, 1 week or more, 1 month or more, or even more. In some instances, the subject methods include evaluating a spatial distribution of fluorescence emissions from a sensor-contacted sample. Any convenient methods of evaluating a sample for spatial distribution of fluorescence emissions can be utilized, including but not limited to fluorescence microscopy methods.

Any convenient supports may be utilized in the subject methods to immobilize the fluorogenic sensor. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support.

In certain embodiments, the method further includes detecting fluorescence from the fluorogenic sensor. Detecting may include exciting the fluorogenic sensor with one or more lasers and subsequently detecting fluorescence emission from the product of the fluorogenic sensor using one or more optical detectors. Detection of the fluorescence can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry.

Fluorescence in a sample can be measured using a fluorimeter. In some cases, excitation radiation, from an excitation source having a first wavelength, passes through excitation optics. The excitation optics cause the excitation radiation to excite the sample. In response, fluorescent adducts of the sensor in the sample emit radiation which has a wavelength that is different from the excitation wavelength. Collection optics then collect the emission from the sample. The device can include a temperature controller to maintain the sample at a specific temperature while it is being scanned.

Illumination sources useful for exciting the fluorogenic sensors of the invention include, but are not limited to, hand-held ultraviolet lamps, mercury arc lamps, xenon lamps, lasers and laser diodes. These illumination sources are optionally integrated into laser scanners, fluorescence microplate readers, standard or mini-fluorometers, or chromatographic detectors. In some instances, fluorogenic sensors of the invention are excitable at or near 335 nm, and can be excited using a relatively inexpensive red laser excitation source. In some embodiments the fluorogenic sensor is excited at or near 335 nm and detected at or near 525 nm.

In some embodiments, the method of evaluating a sample for the presence of a hydrazine analyte further includes detecting fluorescence in a flow cytometer. In some embodiments, the method of evaluating a sample for the presence of a target analyte further includes imaging the fluorogenic sensor-contacted sample using fluorescence microscopy. Fluorescence microscopy imaging can be used to identify the presence of hydrazine in the contacted sample to evaluate whether the hydrazine analyte is present and whether the hydrazine analyte changes over time. Microscopy methods of interest that find use in the subject methods include laser scanning confocal microscopy.

Kits

Aspects of the invention further include kits for use in practicing the subject methods and compositions. The compounds of the invention can be included as reagents in kits for use in, for example, the methodologies described above.

A kit can include a fluorogenic sensor (e.g., as described herein); and one or more components selected from the group consisting of a sensor, a buffer, a solvent, a hydrazine standard and instructions for use.

The one or more components of the kit may be provided in separate containers (e.g., separate tubes, bottles, or wells in a multi-well strip or plate).

The fluorogenic sensors of the kit may be provided in a liquid composition, such as any suitable buffer. Alternatively, the fluorogenic sensors of the kit may be provided in a dry composition (e.g., may be lyophilized), and the kit may optionally include one or more buffers for reconstituting the dry compound. In certain aspects, the kit may include aliquots of the fluorogenic sensors provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The fluorogenic sensors, methods and kits as described herein may find use in a variety of applications, including analysis of various water samples and biological samples, in which the detection and/or analysis of hydrazine is desirable. Methods of the invention find use in a variety of different applications including any convenient application where detection and/or quantitation of hydrazine by fluorescence is of interest. In some instances, the subject sensors find use in detecting and/or quantifying the level of hydrazine in an aqueous sample. Such aqueous samples may include but are not limited to, an environmental water sample, a treated or untreated waste water sample and drinking water sample. In other instances, the subject sensors find use in detecting and/or quantifying the level of hydrazine in a biological fluids e.g. urine.

In some instances, the subject sensors find use in evaluating the diffusion of a hydrazine analyte of interest across a phospholipid membrane. Such applications find use in research applications involving the elucidation of biological processes, e.g., in a cellular sample, where the production and diffusion of a hydrazine analyte is implicated.

EXAMPLES

Example 1: Synthesis of Fluorogenic Sensor Compound 2

Compound 2 was prepared according to Scheme 1:

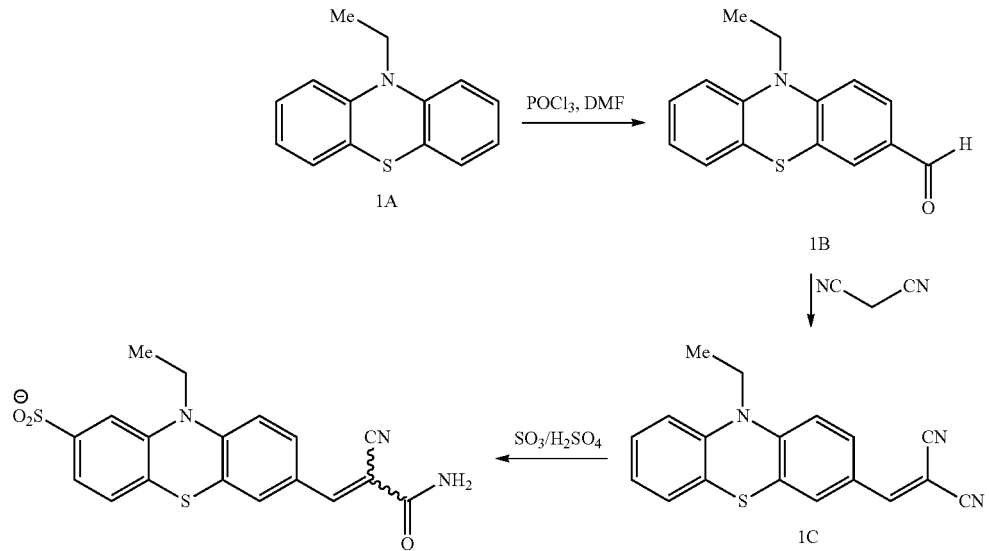

Procedure:

Aldehyde 1B was prepared by treatment of Compound 1A with phosphorus oxychloride in dimethylformamide (DMF) (Vilsmeier-Haak carbonylation reaction).

Compound 1C was synthesized by treatment of aldehyde 1B with malononitrile.

See, e.g., the procedure outlined in: Yang et al. "*A new fluorescent and colorimetric sensor for hydrazine and its application in biological systems*", J. Mater. Chem. B, 2014, 2, 1846. Yang et al. discloses that the Vilsmeier-Haak carbonylation reaction occurs para to the sulfur atom of compound 1A. However, inventors have discovered through NMR experiments and an examination of the literature that the Vilsmeier-Haak carbonylation of 1A proceeds para to nitrogen, not para to sulfur to result in aldehyde 1B.

Phenothiazine Sulfonate 2:

Phenothiazine 1C (160 mg) was dissolved in 5 ml fuming $H_2SO_4$ (20-30% free $SO_3$) at 0° C. under $N_2$. The resulting mixture was warmed to room temperature and stirred for 3 h, after which time the reaction mixture was poured over 300 ml ice in a 500 mL Erlenmeyer flask, rinsed with ice water and filtered through a Hirsch funnel into a vacuum flask. To capture additional crude residue, the filtrate was filtered 3 more times through the same Hirsch funnel, or until the filtrate appeared homogeneous. The Vacuum was pulled on the filter flask until residual ice in the funnel had melted and the crude residue was dry. The rust-colored crude residue on the filter paper was then dissolved and filtered by repeatedly pouring methanol over the residue, agitating with a spatula, and pulling the filtrate into a new vacuum flask. The resulting methanolic filtrate was concentrated slowly on a rotary evaporator. The resulting crude purple/black tar was purified by flash column chromatography on silica gel, 0 to 30% methanol/dichloromethane, followed by preparatory thin layer chromatography, 25% methanol/dichloromethane, to provide the phenothiazine sulfonate hydrazine sensor 2 (22.4 mg, 8.5%) as an orange-red solid.

Physical Properties 2:

$R_f$=0.40 (silica gel, 75:25 DCM:MeOH, visible by eye as a yellow spot);

IR (film) vmax=3442, 2929, 2214, 1673, 1569, 1471, 1410, 1215, 1187, 1138, 1037, 805, 662, 616 cm−1;

$^1$H NMR (500 MHz, Methanol-$d_4$) δ 1.30 (t, J=7.3 Hz, 9H), 1.44 (t, J=7.0 Hz, 3H), 3.18 (q, J=7.3 Hz, 6H), 4.05 (q, J=7.0 Hz, 2H), 7.09 (d, J=8.7 Hz, 1H), 7.14 (d, J=7.9 Hz, 1H), 7.42 (dd, J=7.9, 1.7 Hz, 1H), 7.44 (d, J=1.7 Hz, 1H), 7.73 (d, J=2.2 Hz, 1H), 7.83 (dd, J=8.7, 2.2 Hz, 1H), 8.03 (s, 1H);

$^{13}$C NMR (126 MHz, CD$_3$OD) δ 165.86, 151.57, 149.71, 146.16, 144.12, 132.75, 129.75, 127.87, 127.61, 126.77, 124.87, 122.01, 117.83, 116.27, 114.30, 102.67, 43.42, 12.95;

MS (ESI) m/z calcd. for $C_{18}H_{14}N_3O_4S_2^-$ [M-H]$^-$ 400.0, found 400.1.

Example 2: Detection of Hydrazine in an Aqueous Sample Using Fluorogenic Sensor 2

Scheme 2 illustrates the reaction that takes place when compound 2 (or a salt thereof) is contacted with hydrazine in a sample. Compound 2 is added to an aqueous sample to a concentration of 440 μM or less. If hydrazine is present in the sample, when it comes into contact with an orange solution of compound 2 it reacts with the α,β-unsaturated α-cyanoamide group to produce hydrazal 4 as a colorless solution. Upon excitation at 335 nm, hydrazal 4 fluoresces green at 525 nm.

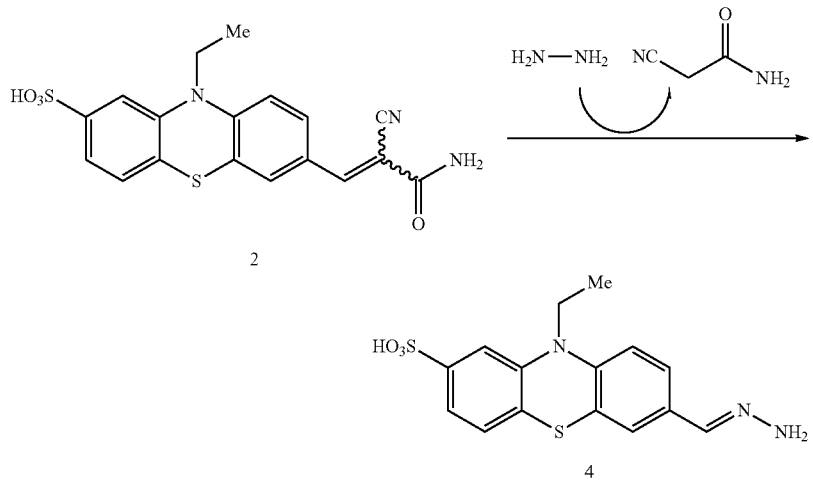

Scheme 2

FIG. 1 illustrates the NMR characterization of the reaction that takes place when compound 2 is contacted with deuterium labelled hydrazine in a sample. The reactions that take place in the NMR characterization experiment are shown in Scheme 3 below.

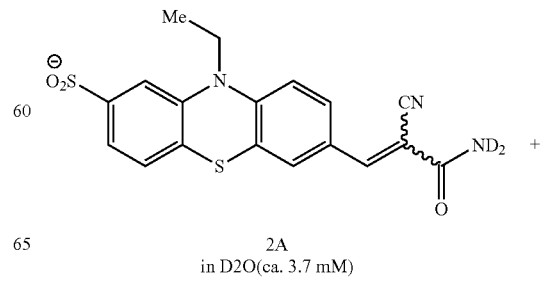

Scheme 3

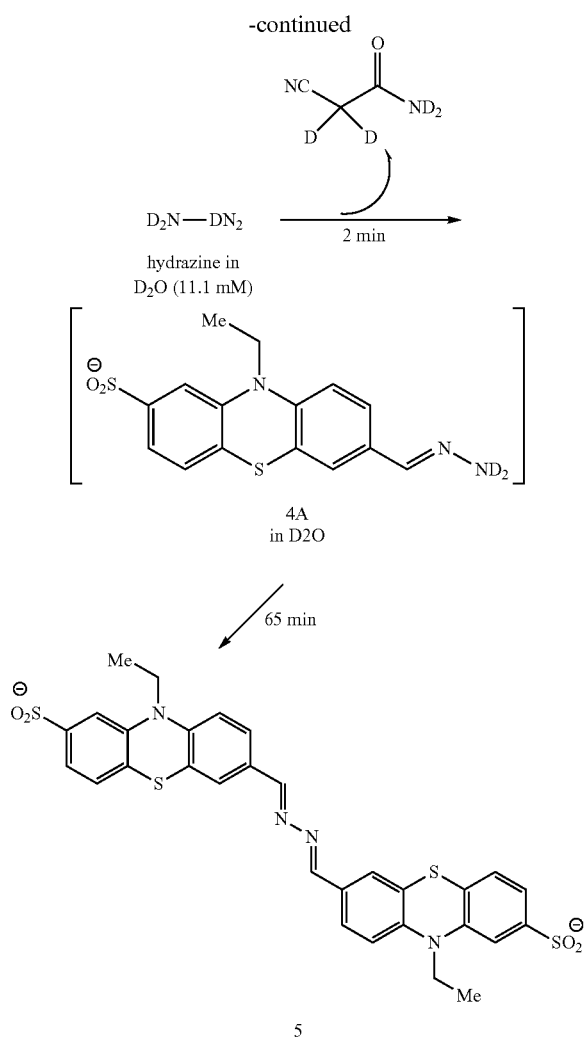

NMR Characterization Procedure:

To a deep orange solution of compound 2A (1.6 mg, ~0.037 mmol) and hydrazine monohydrochloride (0.8 mg, 0.111 mmol) in 1.0 ml $D_2O$ in an NMR test tube under argon was added 40% NaOD in $D_2O$ (30 μL, 0.3 mmol). The test tube head space was filled with argon and the tube was capped and sealed with Parafilm. The reaction was initiated by inverting the tube which was done four times. The mixture immediately began to pale. The tube was inserted into a 600 MHz NMR spectrometer (Varian) and successive 8-scan spectra were taken 40 seconds apart for 30 minutes. At t=30 minutes, a 3-minute lapse in data collection commenced for the preparation of an LCMS sample. Data collection then resumed (40 seconds apart, as before) for an additional 30 minutes. Sample was yellow and fluoresced green under long-wave UV radiation.

Results of NMR Characterization Experiment:

Immediately after raising the pH, all of compound 2A was converted (no compound 2A signal observed at t=2 min, Scheme 2) to an intermediate that was identified by mass spectrometry as hydrazal 4A (m/z obsd.=348.1, calcd.=348.0). Over the course of the NMR experiment, it was observed that hydrazal 4A was converted to azine 5 (m/z obsd.=665.3, calcd.=665.1). When Compound 2A (53 μM) was combined with excess hydrazine (125 mM) in buffer (see FIG. 7), gain of fluorescence was observed at a rapid rate ($t_{1/2}$=1.0 min). Since this fluorescence gain is over an order of magnitude faster than the expected rate of formation of compound 5 from compound 4A, it was deduced that the fluorescence gain observed in the fluorometric assays was due to the formation of Compound 4A. It was hypothesized that at the lower concentration used in the hydrazine transmembrane diffusion assay ([2A]$_0$=420 μM; [4A](t)≤420 μM), compound 4A dimerizes to compound 5 on a slower timescale than that of the experiment.

Figure 2:
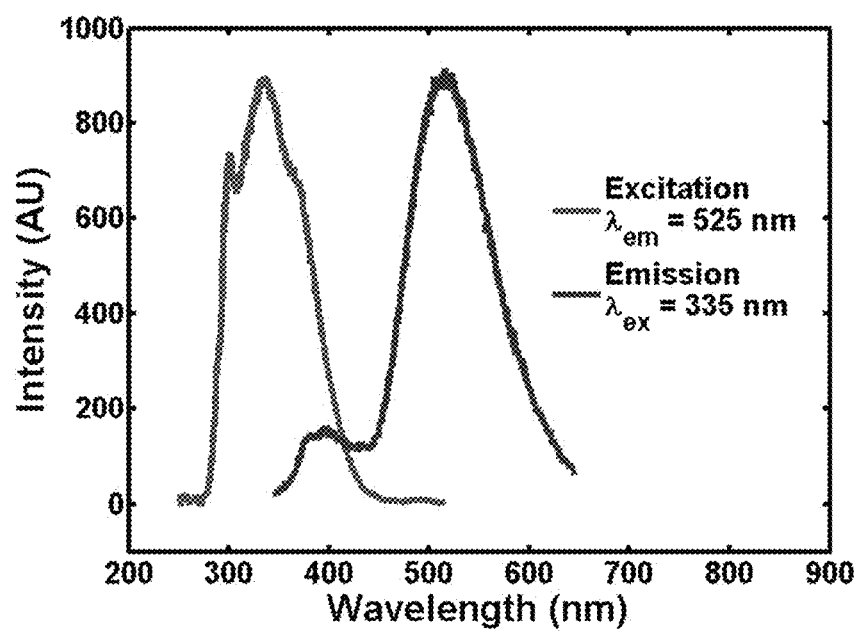
FIG. 2 illustrates fluorescence and fluorescence excitation spectra of hydrazal 4, formed in situ by the reaction of hydrazine sensor, compound 2 with hydrazine. Left curve: fluorescence excitation spectrum with $\lambda_{em}$=525 nm. Right curve: emission spectrum with $\lambda_{ex}$=335 nm.

Fluorescence Spectra:

FIG. 2 illustrates the fluorescence and fluorescence excitation spectra of hydrazal 4 formed in situ by the reaction of compound 2 (45 μM) with hydrazine (50 mM) in 500 mOsM buffer for 1 hour, obtained in 4 mL cuvette (path length=1 cm). Left curve: fluorescence excitation spectra with $\lambda_{em}$=525 nm. Right curve: emission spectrum with $\lambda_{em}$=335 nm.

Example 3: Vesicle Encapsulation and Membrane Interaction Evaluation

In order to evaluate whether compound 2 can be encapsulated in vesicles and whether compound 2 is localized in the aqueous interior of vesicles or membrane bound, hydrazal 4 was encapsulated in [5][3]PC GUVs (ladderane lipid giant unilamellar vesicles). Hydrazal 4 was used in this experiment because compound 2 has very little fluorescence. Hydrazal 4 was generated by reacting 850 μM compound 2 with 8.5 mM hydrazine in degassed water overnight. A Leica DMI6000 B epifluorescence microscope equipped with a 63× oil immersion objective (Leica Microsystems, Buffalo Grove, Ill., USA), pco.edge sCMOS (PCO, Kelheim, Lower Bavaria, Germany) camera, DAPI filter cube (ex=387/1 nm, bs=344-404/415-570 nm, em=447/60 nm), and Texas Red filter cube (ex=560/40, bs=595, em=645/75) was used to image these vesicles. Images were false colored and merged to examine localization of the two dyes.

Figure 3:
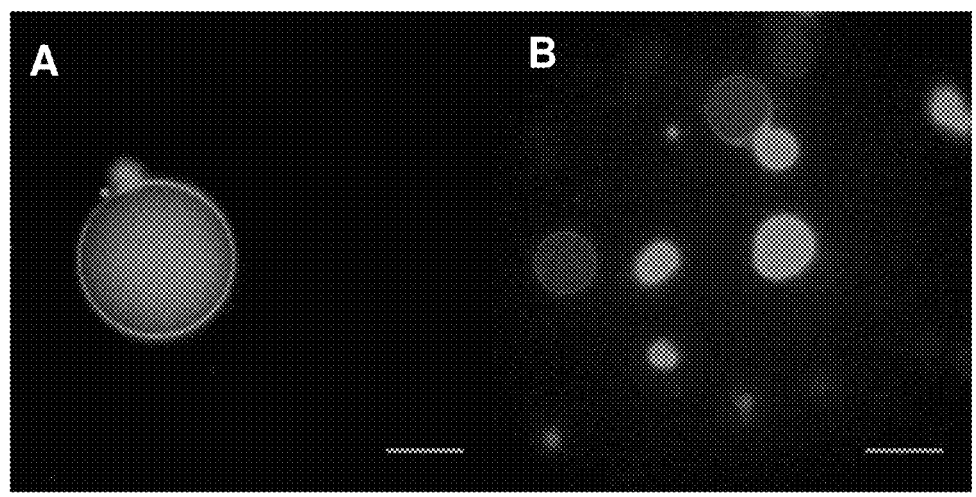
FIG. 3 (panels A and B) show fluorescence images of [5][3]PC GUVs encapsulating hydrazal 4. Panels A and B show hydrated [5][3]PC (0.1 mol % Texas Red-DHPE (pale grey) encapsulating 420 µM hydrazine adduct, compound 4 (dark grey) incubated at 37° C. then cooled to room temperature. The horizontal white lines in panels A and B indicate a scale of 25 um.

Results:

FIG. 3 (panels A and B) show fluorescence images of [5][3]PC GUVs encapsulating Compound 4. Panels A and B show Hydrated [5][3]PC (0.1 mol % Texas Red-DHPE (pale grey) encapsulating 420 μM compound 4 (dark grey) incubated at 37° C. then cooled to room temperature. These results show that the fluorescence of hydrazal 4 is clearly localized to the interior of the GUVs, proving that this molecule can be encapsulated and that it does not strongly interact with lipid bilayers.

Example 4: Kinetic Experiments (i) Lipid-Free Kinetic Run Assay

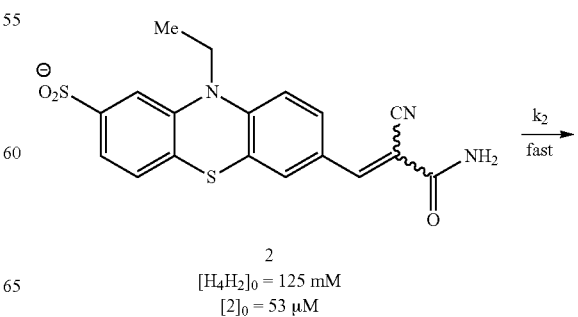

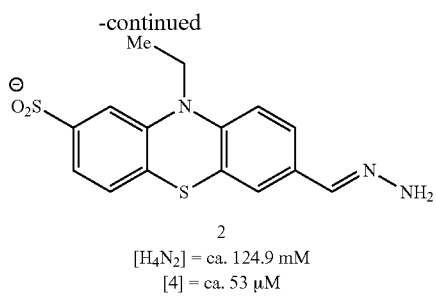

2
[H₄N₂] = ca. 124.9 mM
[4] = ca. 53 μM

Procedure:

Under argon, 250 μL of compound 2 (420 μM) was added to 750 μL degassed 50 mM phosphate buffer and mixed by pipette aspiration; this 1 mL solution was added to 1 mL hydrazine buffer in a cuvette under argon; the mixture was mixed by aspiration, and then a fluorometric kinetic trace was acquired at $\lambda_{ex}$=335 nm and $\lambda_{em}$=525. Rapid pseudo-first order kinetics were observed with $t_{1/2}$ of approximately 1 min.

(ii) Vesicles Ruptured with Triton X-100 Assay

Figure 4:
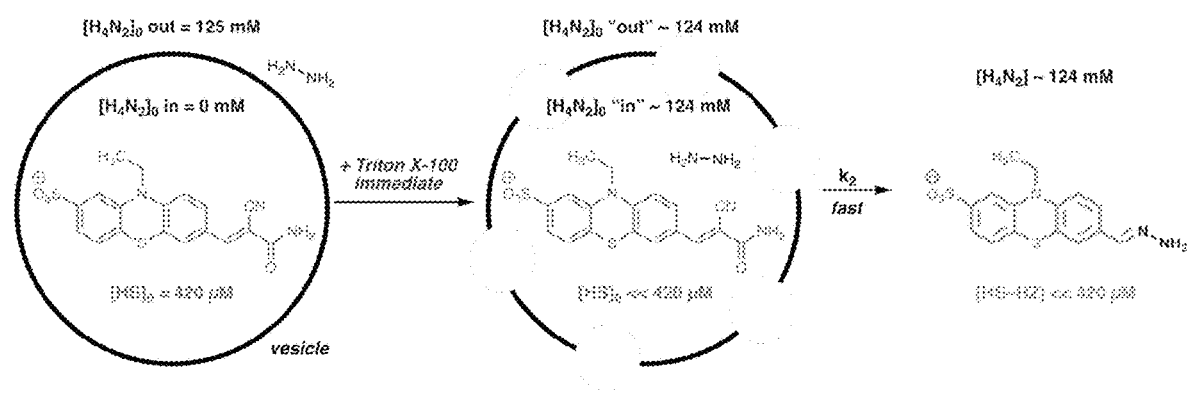
FIG. 4 illustrates the reaction kinetics that take place when hydrazine diffuses across a phospholipid membrane (vesicle), comes into contact with compound 2, and the vesicles are ruptured with Triton X-100 to release hydrazal 4.

FIG. 4 depicts the kinetic run with ruptured vesicles. Note: "HS" refers to compound 2 and "HS-HZ" refers to compound 4. More specifically, FIG. 4 illustrates the reaction kinetics that takes place after addition of the detergent Triton X-100 to vesicles with encapsulated compound 2 in hydrazine buffer.

Procedure:

SOPC SUVs (1-Stearoyl-2-oleoyl-sn-glycero-3-phosphocholine small unilamellar vesicles) with encapsulated 420 μM Compound 2 in degassed 50 mM phosphate buffer were prepared and purified according to the procedure set out in Example 5 below. Under argon, the vesicles (1 mL) were added to 1 mL hydrazine buffer in a cuvette under argon; the mixture was mixed with pipette aspiration; 30 μL of 10% Triton X-100 in H₂O (v/v) was added to the mixture, which was mixed by aspiration under argon and then capped with parafilm before acquiring a fluorometric kinetic trace at $\lambda_{ex}$=335 nm and $\lambda_{em}$=525.

(iii) Hydrazine Diffusion into Vesicles Assay

Figure 5:
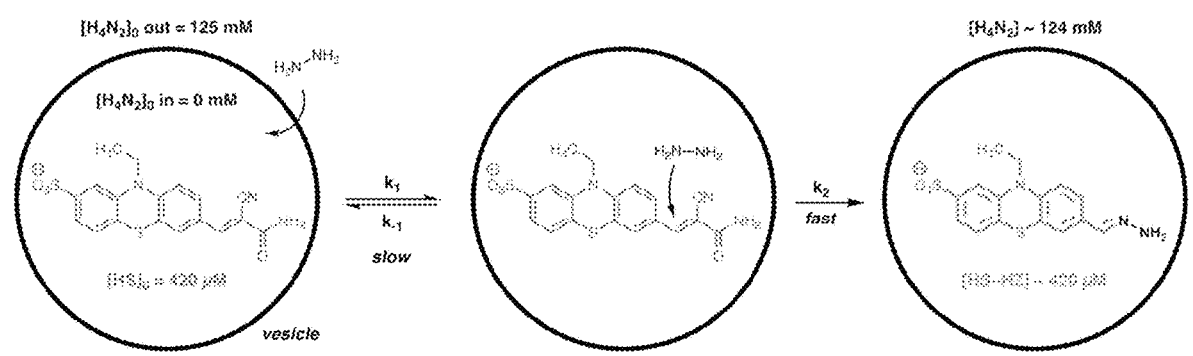
FIG. 5 illustrates the reaction kinetics that take place when hydrazine diffuses across a phospholipid membrane (vesicle) in intact vesicles. The left panel of FIG. 5 depicts the slow transmembrane diffusion of the hydrazine. The middle and right panels depict the fast reaction of the hydrazine with compound 2 in intact vesicles.

FIG. 5 illustrates the kinetic run with intact vesicles. The hydrazine diffusion experiment was carried out according to Example 5 below. The left panel of FIG. 5 depicts the slow transmembrane diffusion of the hydrazine. The middle and right panels depict the fast reaction of the hydrazine with compound 2.

(iv) Compound 4 Leakage Assay

Figure 6:
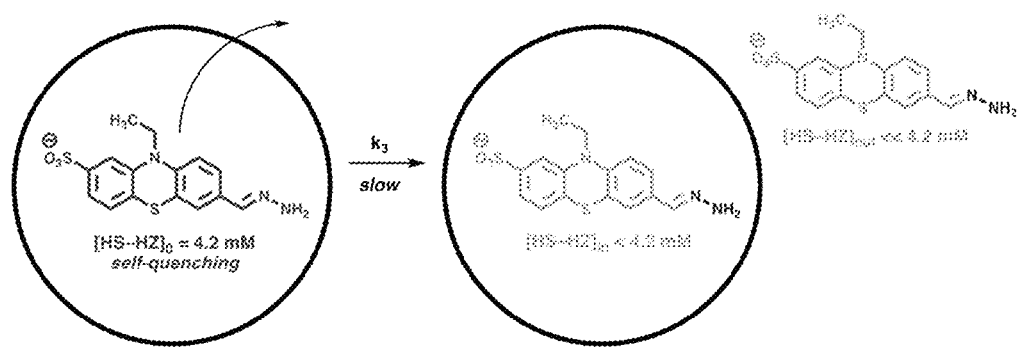
FIG. 6 illustrates the slow diffusion of hydrazal 4, out of vesicles.

FIG. 6 illustrates the diffusion of compound 4 out of vesicles. Note: at 4.2 mM, some dimerization (e.g., to form compound 5) is likely to occur on the time course of this experiment. It was hypothesized that the lower hydrophilicity of the dimer 5 results in faster leakage than for hydrazal 4, so that this experiment gives an upper bound on the hydrazal 4 leakage rate.

Procedure:

Under argon, 422 μL hydrazine buffer was added to 0.72 mg of compound 2 in a vial and then incubated at room temperature for 30 min under argon to make a 0.72 mg/401.5 mg mmol⁻¹/0.422 mL=4.2 mM solution of compound 4. A 0.5-mg film of POPC (phosphatidylcholine) under argon was hydrated with 250 μL of 4.2 mM hydrazal 4, vortexed vigorously for ≥10 sec, and extruded 31 times through a 50 nm-pore polycarbonate membrane before purification on a size exclusion column run under argon with degassed 50 mM phosphate buffer. To assess maximum intensity (100% diffusion) for the sample, 0.5 mL vesicles were ruptured with 30 μL 10% Triton X-100 in H₂O (v/v) and added to 1.5 mL degassed 50 mM phosphate buffer; this sample was inserted into the fluorimeter and a kinetic trace at $\lambda_{ex}$=335 nm and $\lambda_{em}$=525 was obtained for 5 min. A new sample was then prepared by adding 0.5 mL vesicles to 1.5 mL degassed 50 mM phosphate buffer and collecting a kinetic trace for 12 h. After the run was over, 30 μL 10% Triton X-100 in H₂O (v/v) was added to the sample to rupture the vesicles to verify the maximum intensity (100% diffusion). This value agreed well with the value obtained before the leakage experiment (178±1 vs. 172.2±0.9 arbitrary units). The dequenching leakage $t_{1/2}$ was obtained by linear fit of the logarithm using the average maximum intensity value obtained between the two rupturing experiments (175 arbitrary units).

Results:

The reaction of compound 2 with excess N₂H₄ at 125 mM had a much shorter $t_{1/2}$ (1.0 min; 5.3 min in the presence of lipid and detergent) than that of compound 2 encapsulated within SUVs composed of 18:0-18:1 PC (SOPC) ($t_{1/2}$=50.7 min). Leakage from SUVs of the hydrazal 4 is negligible on the timescale of hydrazine transmembrane diffusion, suggesting that compound 2 leakage is also negligible on this timescale (FIG. 7).

Figure 7:
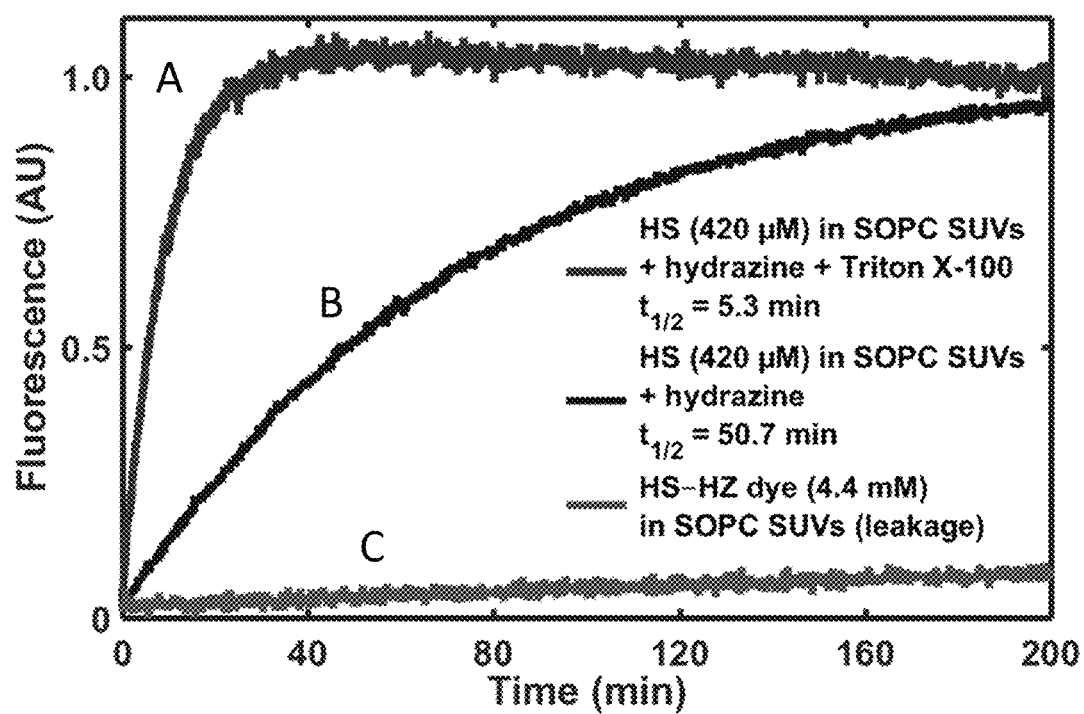
FIG. 7 illustrates the fluorescence of the hydrazine sensor (compound 2) as a function of time in the ruptured vesicle hydrazine diffusion assay (line A), intact vesicle hydrazine diffusion assay (line B) and hydrazal 4 leakage assay (line C).

FIG. 7 illustrates the fluorescence of the hydrazine sensor (compound 2) as a function of time in the ruptured vesicle hydrazine diffusion assay (line A), intact vesicle hydrazine diffusion assay (line B) and hydrazal (compound 4) leakage assay (line C). Since the concentration of dye is higher in the compound 4 leakage assay (iv) than in the hydrazine diffusion assay (iii), this provides an upper bound for the dye leakage rate during the hydrazine diffusion assay. Sensor leakage is assumed to be similar. When 18:0-18:1 PC (SOPC) SUVs encapsulating compound 2 were added to 125 mM N₂H₄ and ruptured, a much faster fluorescence increase ($t_{1/2}$=5.3 min) was observed than when intact SOPC SUVs encapsulating compound 2 were incubated in 125 mM N₂H₄. Compound 4 dye leakage out of 18:0-18:1 PC (SOPC) SUVs, measured by a dequenching assay, is negligible over the course of N₂H₄ transmembrane diffusion.

Figure 8:
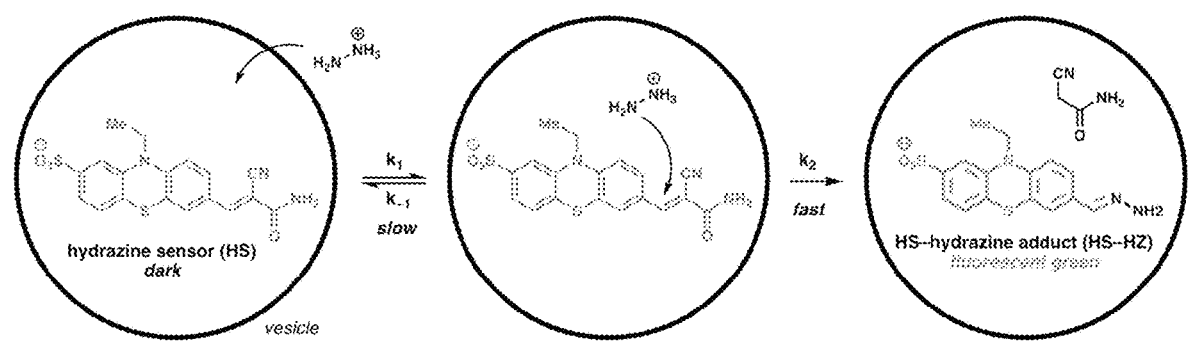
FIG. 8 further illustrates the reaction that takes place when hydrazine diffuses across a phospholipid membrane and comes into contact with compound 2.

FIG. 8 further illustrates the reaction that takes place when hydrazine diffuses across a phospholipid membrane and comes into contact with compound 2.

Example 5: Hydrazine Diffusion Assay Procedure

A. Lipid Film Preparation:

1.0 mg of phosphatidylcholine lipid in chloroform solution was dispensed into a 20 mL scintillation vial, dried under a stream of Ar, and put under house vacuum in a desiccator overnight. The vial was then removed from the desiccator, purged of air with a stream of Ar, closed, and sealed with Parafilm.

B. 50 mM Phosphate Buffer Preparation:

6.0 g of monobasic sodium phosphate was dissolved in 1 L MilliQ water to make a 50 mM solution. The pH of the solution was raised to 7.40 by addition of 5N NaOH (typically 9 mL). Depending on the amount of NaOH added, NaCl was added (typically 10 g) to form a 500 mosM buffer.

C. Removal of O₂ from Water and Buffer:

Loosely capped Falcon tubes containing 45 ml of buffer or MilliQ water were placed in a desiccator and put under house vacuum overnight. The desiccator was then filled with Ar by first capping the inlet with a rubber septum, then piercing the septum with two Ar-filled balloons with attached needles, then simultaneously closing the desiccator valve to vacuum and opening the desiccator valve to the inlet. The desiccator top was then removed and the Falcon tubes quickly closed and sealed with Parafilm.

D. Hydrazine Buffer Preparation:

425-430 mg of hydrazine hydrochloride was weighed and dispensed into a 25 ml reagent bottle pre-filled with Ar; the bottle was then purged of air with a stream of Ar and closed. 25 ml degassed MilliQ water was added to the bottle, along with 300 µl 5N NaOH, under a stream of Ar. The bottle was closed and shaken vigorously. The pH was then adjusted to 7.40±0.02 with 5N NaOH, purging of air with Ar immediately after each pH measurement with a glass electrode. The bottle was purged of air with a stream of Ar, closed, and sealed with Parafilm.

E. Size Exclusion Column Preparation:

A suspension of Sepharose® CL-4B in 10-30% ethanol (Sigma) was added to an 8.5-cm size-exclusion column. Methanol was washed out of the column by flushing with at least 5 column volumes of 50 mM phosphate buffer (described above, section B). Then the column was capped with a rubber septum, the septum was pierced with an Ar-filled balloon with attached needle, and the column was run until the meniscus descended to the top of the resin. Then, under a stream of Ar, the head space was filled with degassed buffer (described above, section C) and the Falcon tube containing the degassed buffer was purged of any incidental air with a stream of Ar, then closed. Using this technique, the column was purged of oxygenated buffer by running at least 5 column volumes of degassed buffer through the column under Ar.

F. Film Hydration and Extrusion to Form 90-130-nm SUV's:

An Avanti Mini Extruder (Avanti Polar Lipids, Alabaster, Ala.) was equipped with a 50 nm-pore polycarbonate membrane. 250 µl degassed phosphate buffer was passed through the extruder 9 times to remove bubbles and check for leaks. 250 µl of 440 µM hydrazine sensor 2 was added to the lipid film under a stream of Ar and the mixture was agitated for 0 seconds on a Vortex agitator at full power. In the case of ladderanes, which were resistant to suspension, the sample was additionally agitated in an ultrasonic bath for seconds. The cloudy yellow suspension was passed through the extruder 31 times.

G. Vesicle Purification by Size Exclusion Chromatography:

The vesicles were loaded onto the column under a stream of Ar and then degassed phosphate buffer was added to the column under a stream of Ar; the column was subsequently run under Ar. Effluent was collected in a 4 ml polyacrylamide cuvette that was under a continuous stream of Ar. Vesicles were not visible by eye or upon exposure to a UV lamp; vesicles were detected by directing the beam from a 5 mW green laser pointer horizontally through the cuvette; upon elution of the vesicles, bright scattering was visible. Collected vesicle sample was capped with Parafilm.

H. Fluorimetric Kinetic Hydrazine Diffusion Measurement:

Under an Ar stream, 1.0 ml of hydrazine buffer was dispensed into a 4 ml polyacrylamide cuvette pre-filled with Ar and capped with Parafilm. Under an Ar stream, vesicles were mixed by aspirating with a 1 ml micropipette (3×), then 1.0 ml vesicles were added to the 1.0 ml of hydrazine buffer. After mixing by aspirating with the 1 ml micropipette (3×) under a stream of Ar, the cuvette was carefully closed with Parafilm and inserted into a fluorimeter with excitation wavelength 335 nm, excitation wavelength 525 nm, slit widths 5 nm, data interval 0.04 min, experiment length 300 min. The first 5 min of acquisition were discarded to allow for equilibration of the sample.

I. Data Analysis:

Data were fit to the equation $y=a-b*\exp(c*x)$ using the cftool module in Matlab. The constant c represents the rate constant $k_{obs}$; the half-life $t_{1/2}$ was calculated using the equation $t_{1/2}=\ln(2)/k_{obs}$.

Example 6: Effect of pH on Hydrazine Transmembrane Diffusion

Given that the pH of the interior of the anammoxosome is thought to be approximately 6.3, the hydrazine transmembrane diffusion assay was repeated at pH=6.3. The results are summarized in Table 1 below.

TABLE 1

| comparison of hydrazine transmembrane diffusion rates at pH = 7.40 and 6.30. | | |
|---|---|---|
| Lipid | $N_2H_4$ Diff. $t_{1/2}$ (min) pH = 7.40 | $N_2H_4$ Diff. $t_{1/2}$ (min) pH = 6.30 |
| 18:0-18:1 PC (SOPC) | 50.5 ± 0.5 | 96 ± 23 |
| di22:1 PC (DEPC) | 98.9 ± 6.0 | 583 ± 25 |
| [3][3]PC | 71.5 ± 2.0 | 265 ± 5 |

At pH=6.3, transmembrane diffusion rates are slowed. Lowering the pH decreases the fraction of neutral hydrazine molecules, which likely diffuse across the bilayer faster than protonated hydrazine. While absolute transmembrane diffusion rates change with pH, the trend does not. At both pH levels, ladderane PC bilayers have transmembrane diffusion half-lives that are similar to those of conventional straight chain PCs.

Example 7: Hydrazine Transmembrane Diffusion

Figure 9:
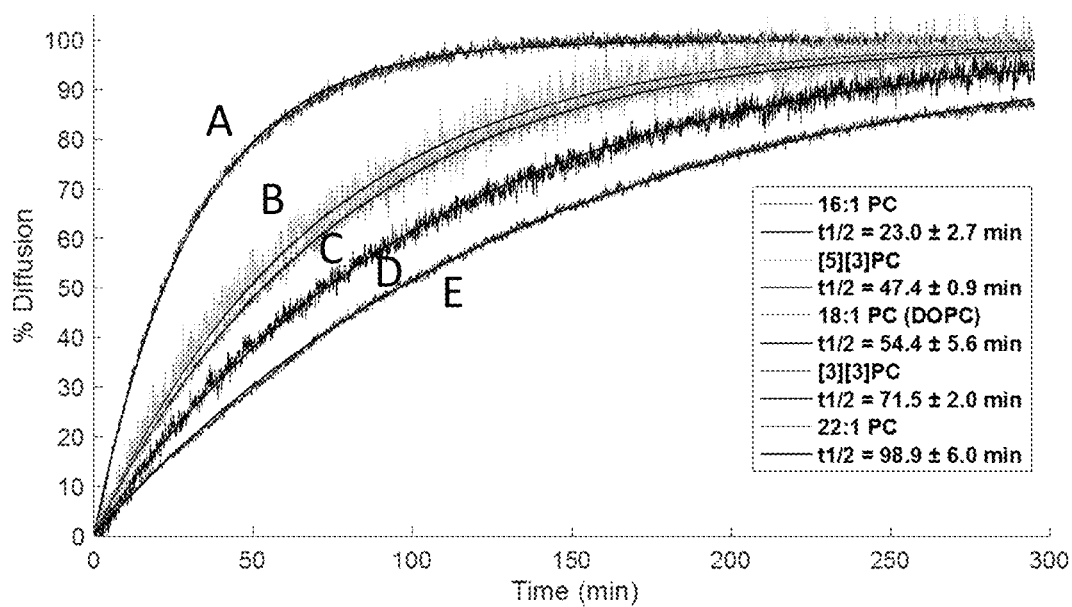
FIG. 9 illustrates hydrazine diffusion across a phospholipid membrane as a function of time for various phosphatidylcholine lipids (PC). Line A depicts 16:1 PC, t ½=23.0+/−2.7 min. Line B depicts [5][3]PC, t ½=47.4+/−0.9 min. Line C depicts 18:1 PC (DOPC), t ½=54.4+/−5.6 min. Line D depicts [3][3]PC, t ½=71.5+/−2.0 min. Line E depicts 22:1 PC, t ½=98.9+/−6.0 min.
Figure 10:
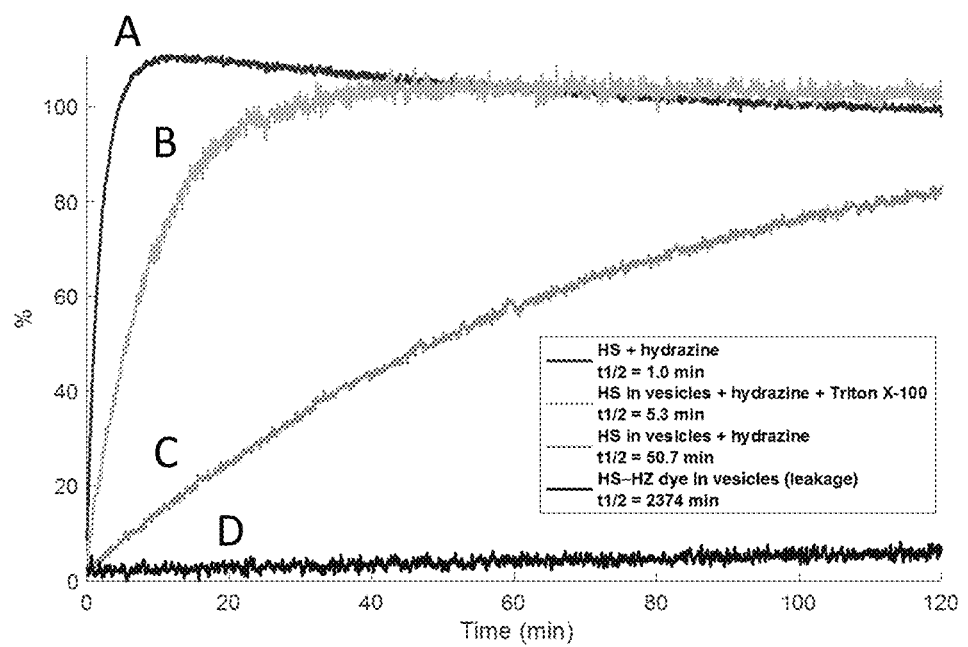
FIG. 10 illustrates the hydrazine diffusion assay as percentage of hydrazine diffusion across a phospholipid membrane as a function of time. Line A depicts the reaction kinetics for a mixture of compound 2 (55 µM) hydrazine (125 mM), t ½=1.0 min. Line B depicts 250 µl vesicles with 440 µM compound 2 encapsulated, added to 2 ml buffer with 125 mM hydrazine, t ½=50.7 min. Line C depicts 250 µl vesicles with 440 µM compound 2 encapsulated, added to 2 ml buffer with 125 mM hydrazine and 30 µl 10% Triton X-100 to rupture vesicles, t ½=5.3 min. Line D depicts dye leakage in 250 µl vesicles with 440 µM compounds 2 encapsulated, added to 2 ml buffer, t ½=2374 min.

The results of the hydrazine diffusion measurements for representative straight-chain lipids and ladderane lipids are depicted in FIG. 9. These results show that hydrazine transmembrane diffusion rates depend on hydrophobic tail length.

More specifically, FIG. 9 illustrates hydrazine diffusion across a phospholipid membrane as a function of time for various phosphatidylcholine lipids (PC). Line A depicts 16:1 PC, t ½=23.0+/−2.7 min. Line B depicts [5][3]PC, t ½=47.4+/−0.9 min. Line C depicts 18:1 PC (DOPC), t ½=54.4+/−5.6 min. Line D depicts [3][3]PC, t ½=71.5+/−2.0 min. Line E depicts 22:1 PC, t ½=98.9+/−6.0 min.

It was observed that ladderane membranes (e.g., with hydrophobic tails that are each 14 carbons long) are less permeable than the conventional straight chain 16:1 PC membrane.

Example 8: Small-Angle X-Ray Scattering (SAXS)

To determine the relevance of bilayer thickness to permeability, small-angle X-ray scattering (SAXS) was performed on rigorously extruded SUV's of unsaturated straight-chain PCs and ladderane PCs (e.g., 16:1 PC, 18:1 PC, [3][3]PC and 22:1 PC).

Figure 11:
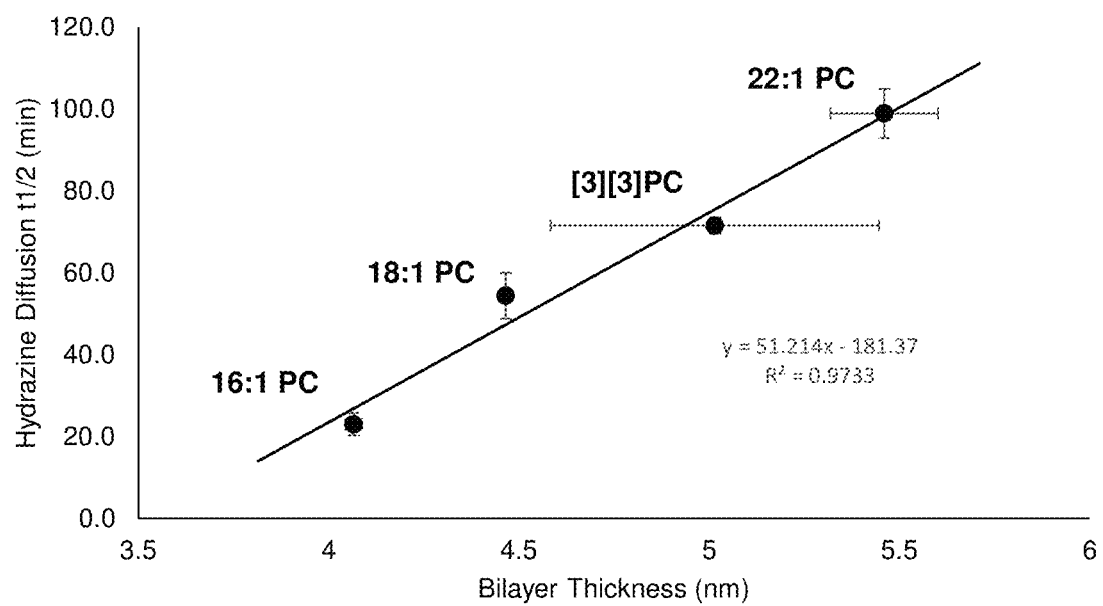
FIG. 11 illustrates the hydrazine diffusion half life for various PC lipids as a function of bilayer thickness.

The results of the Hydrazine diffusion half-life versus thickness as measured by SAXS are depicted in FIG. 11. It was observed that the thickness of unsaturated straight-chain PC bilayers correlates linearly with hydrazine diffusion half-life and that the ladderane membrane [3][3]PC lies neatly along this line.

Accordingly, the SAXS data suggests that ladderane PCs form membranes that are equally as permeable to hydrazine as a straight-chain lipid membrane of the same bilayer thickness.

Notwithstanding the appended claims, the disclosure set forth herein is also described by the following clauses.

Clause 1. A water soluble compound of formula (I):

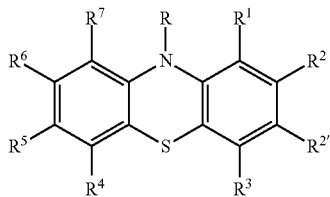

(I)

wherein:

$R^1$ and $R^3$ are independently selected from H, alkyl, substituted alkyl, halogen, carboxy, sulfonate, phosphonate, carboxylate, cyano, hydroxyl, carboxyamide and sulfonamide;

$R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine-reactive group;

$R^4$, $R^5$, $R^6$, $R^7$ are independently selected from H, sulfonate, phosphonate, carboxy, halogen, alkyl, substituted alkyl, cyano, hydroxyl, carboxyamide, sulfonamide and carboxylate; and R is alkyl or substituted alkyl;

wherein at least one of $R^1$-$R^7$ is a water soluble group and at least one of $R^2$-$R^{2'}$ is a hydrazine-reactive group or a salt thereof.

Clause 2. The water soluble compound according to clause 1, wherein at least one of $R^4$, $R^5$, $R^6$ and $R^7$ is —SO$_3$H.

Clause 3. The water soluble compound according to clause 1, wherein at least two or more of $R^4$, $R^5$, $R^6$ and $R^7$ is —SO$_3$H.

Clause 4. The water soluble compound according to clause 1, wherein $R^6$ is —SO$_3$H.

Clause 5. The water soluble compound according to any one of clauses 1 to 4, wherein $R^2$ or $R^{2'}$ is —C=C($R^8$)($R^9$) or an aldehyde, wherein $R^8$ and $R^9$ are each independently selected from the group consisting of CN, C(O)O$R^{10}$, C(O)NR$^{11}_2$ and C(O)$R^{10}$, wherein $R^{10}$ is alkyl, substituted alkyl, aryl or substituted aryl and $R^{11}$ are each independently H, alkyl, substituted alkyl, aryl or substituted aryl.

Clause 6. The water soluble compound according to any one of clauses 1 to 5, wherein R is ethyl.

Clause 7. The water soluble compound according to clause 1, of the formula (IA):

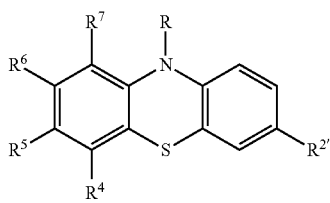

(IA)

wherein:

$R^{2'}$ is a hydrazine reactive group;

$R^4$, $R^5$, $R^6$, $R^7$ are independently selected from H, sulfonate, phosphonate, carboxy, halogen, alkyl, substituted alkyl, cyano, hydroxyl, carboxyamide, sulfonamide and carboxylate; and R is alkyl or substituted alkyl;

wherein at least one of $R^1$-$R^7$ is a water soluble group, or a salt thereof.

Clause 8. The water soluble compound according to clause 1, of the formula (IB):

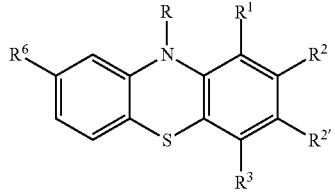

(IB)

wherein:

$R^1$ and $R^3$ are independently selected from H, alkyl, substituted alkyl, halogen, carboxy, sulfonate, phosphonate, carboxylate, cyano, hydroxyl, carboxyamide and sulfonamide;

$R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine reactive group;

$R^6$ is a water soluble group; and

R is alkyl or substituted alkyl;

wherein at least one of $R^2$-$R^2$ is a hydrazine reactive group, or a salt thereof.

Clause 9. The water soluble compound according to clause 1, of the formula (IC):

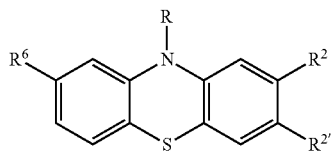

(IC)

wherein:

$R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine reactive group;

$R^6$ is a water soluble group; and

R is alkyl or substituted alkyl;

wherein at least one of $R^2$-$R^2$ is a hydrazine reactive group, or a salt thereof.

Clause 10. The water soluble compound according to clause 1, of the formula (ID):

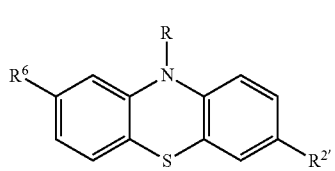

(ID)

wherein:

$R^{2'}$ is a hydrazine reactive group;

$R^6$ is a water soluble group; and

R is alkyl or substituted alkyl, or a salt thereof.

Clause 11. The water soluble compound according to any one of clauses 1 to 10, having the formula

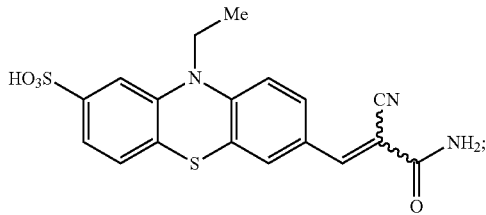

or a salt thereof.

Clause 12. The water soluble compound according to clause 11, wherein the alkene is the E isomer.

Clause 13. The water soluble compound according to clause 11, wherein the alkene is the Z isomer.

Clause 14. The water soluble compound according to any one of clauses 1-10, having the formula

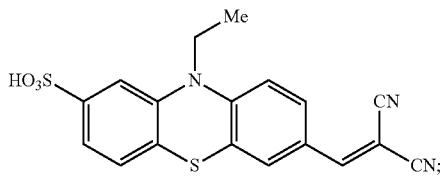

or a salt thereof.

Clause 15. A method of detecting a hydrazine analyte in a sample, comprising:

contacting a sample with the water soluble compound according to any one of clauses 1 to 14 under conditions sufficient to react the hydrazine analyte, if present, with the compound to produce a fluorescent adduct;

detecting the fluorescence of the adduct.

Clause 16. The method according to clause 15, wherein the detecting comprises detecting a change in intensity of fluorescence emitted from the sample.

Clause 17. The method according to clause 16, wherein the change in intensity of fluorescence emitted is detected at 525 nm.

Clause 18. The method according to claim 15, wherein the water soluble compound reacts with the hydrazine analyte to produce the fluorescent adduct in a colorless solution which fluoresces green when exposed to UV light.

Clause 19. The method according to clause 15, wherein reaction with the hydrazine analyte to produce a colorless solution is complete in 1 hour or less.

Clause 20. The method according to any one of clauses 15 to 19, wherein the hydrazine analyte is detected at neutral pH.

Clause 21. The method according to any one of clauses 15 to 19, wherein the hydrazine analyte is detected at room temperature.

Clause 22. The method according to any one of clauses 15 to 19, wherein the level of hydrazine analyte in the sample is quantitatively determined.

Clause 23. The method according to any one of claims 15 to 19, wherein the sample is a water sample.

Clause 24. The method according to clause 23 wherein the water sample is an environmental water sample.

Clause 25. The method according to clause 23, wherein the water sample is a sample of drinking water.

Clause 26. The method according to any one of clauses 15 to 19, wherein the sample is a biological sample.

Clause 27. The method according to clause 26, wherein the biological sample is urine.

Clause 28. The method according to any one of clauses 15 to 19, wherein the water soluble compound is added to the sample in a concentration of 440 µM or less.

Clause 29. A method of detecting hydrazine diffusion across a phospholipid membrane comprising:

contacting a cell with the water soluble compound according to any one of clauses 1 to 14;

detecting a variation of an intensity of fluorescence emitted by the compound when the cell is exposed to hydrazine in a medium which diffuses across the cell membrane.

Clause 30. The method according to clause 29, wherein the hydrazine in the cell is generated by a known drug.

Clause 31. The method according to clause 29, wherein the phospholipid membrane comprises ladderane membranes.

Clause 32. The method according to clause 29, wherein the hydrazine diffusion across the phospholipid membrane is quantitatively determined.

Clause 33. The method according to clause 29, wherein the water soluble compound does not interfere with the phospholipid membrane.

Clause 34. A kit for analyzing a sample, comprising:

the water soluble compound according to any one of clauses 1 to 14; and an additional component selected from a sensor, a buffer, a solvent, a hydrazine standard and instructions for use.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A water soluble compound of formula (I):

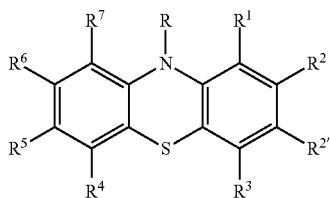

wherein:
- $R^1$ and $R^3$ are independently selected from H, alkyl, substituted alkyl, halogen, carboxy, sulfonate, phosphonate, carboxylate, cyano, hydroxyl, carboxyamide and sulfonamide;
- $R^2$ and $R^{2'}$ are independently selected from H, alkyl, substituted alkyl, halogen, carboxy, sulfonate, phosphonate, carboxylate, cyano, hydroxyl, carboxyamide, sulfonamide and a hydrazine-reactive group;
- $R^4$, $R^5$, $R^6$, $R^7$ are independently selected from H, sulfonate, phosphonate, carboxy, halogen, alkyl, substituted alkyl, cyano, hydroxyl, carboxyamide, sulfonamide and carboxylate; and
- R is alkyl or substituted alkyl;
- wherein at least one of $R^1$ and $R^3$-$R^7$ is a water soluble group and at least one of $R^2$—$R^{2'}$ is a hydrazine-reactive group, wherein the hydrazine-reactive group is selected from the group consisting of a disubstituted alkene, a phenyl acetate, an O-acyl phenol, and an aldehyde, wherein the alkene is substituted with two groups independently selected from a nitrile, an ester, an amide and a ketone, or a salt thereof.

2. The water soluble compound according to claim 1, wherein at least one of $R^4$, $R^5$, $R^6$ and $R^7$ is —SO$_3$H.

3. The water soluble compound according to claim 1, wherein $R^6$ is —SO$_3$H.

4. The water soluble compound according to claim 1, wherein $R^2$ or $R^{2'}$ is —CH=C($R^8$)($R^9$) or an aldehyde, wherein $R^8$ and $R^9$ are each independently selected from the group consisting of CN, C(O)OR$^{10}$, C(O)NR$^{11}{}_2$ and C(O)R$^{10}$, wherein $R^{10}$ is alkyl, substituted alkyl, aryl or substituted aryl and $R^{11}$ are each independently H, alkyl, substituted alkyl, aryl or substituted aryl.

5. The water soluble compound according to claim 1, wherein R is ethyl.

6. The water soluble compound according to claim 1, having the formula

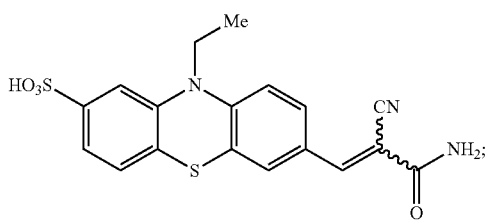

or a salt thereof.

7. The water soluble compound according to claim 6, wherein the alkene is the E isomer.

8. The water soluble compound according to claim 6, wherein the alkene is the Z isomer.

9. The water soluble compound according to claim 1, having the formula

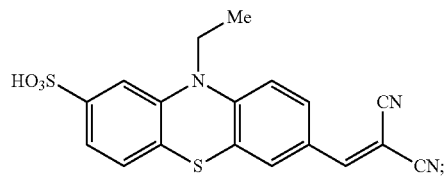 [SMILES: CCN1c2ccc(C=C(C#N)C#N)cc2Sc2ccc(S(=O)(=O)O)cc21]

or a salt thereof.

10. A method of detecting a hydrazine analyte in a sample, comprising:
- contacting a sample with the water soluble compound according to claim 1 under conditions sufficient to react the hydrazine analyte, if present, with the compound to produce a fluorescent adduct;
- detecting the fluorescence of the adduct.

11. The method according to claim 10, wherein the detecting comprises detecting a change in intensity of fluorescence emitted from the sample.

12. The method according to claim 11, wherein the change in intensity of fluorescence emitted is detected at 525 nm.

13. The method according to claim 10, wherein the hydrazine analyte is detected at neutral pH.

14. The method according to claim 10, wherein the hydrazine analyte is detected at room temperature.

15. The method according to claim 10, wherein the level of hydrazine analyte in the sample is quantitatively determined.

16. The method according to claim 10, wherein the sample is a water sample.

17. The method according to claim 10, wherein the sample is a biological sample.

18. A method of detecting hydrazine diffusion across a phospholipid membrane comprising:
- contacting a cell with the water soluble compound according to claim 1;
- detecting a variation of an intensity of fluorescence emitted by the compound when the cell is exposed to hydrazine in a medium which diffuses across the cell membrane.

19. The method according to claim 18, wherein the hydrazine in the cell is generated by a known drug.

20. The method according to claim 18, wherein the phospholipid membrane comprises ladderane membranes.

21. The water soluble compound according to claim 1, wherein the hydrazine reactive group is a disubstituted alkene, substituted with a malononitrile group, a malonate ester group or a malonate amide group.

22. The water soluble compound according to claim 1, wherein the hydrazine reactive group is an α,β-unsaturated α-cyanoamide group.

23. The water soluble compound according to claim 1, wherein the hydrazine reactive group is an α,β-unsaturated malononitrile group.

* * * * *